United States Patent [19]

Gerber

[11] Patent Number: 5,562,899
[45] Date of Patent: Oct. 8, 1996

[54] MEDICAL PREVENTION OF LACERATIONS TO THE VAGINA AND PERINEUM

[76] Inventor: Allen Gerber, 42 Nutmeg Rd., High Falls, N.Y. 12440

[21] Appl. No.: 395,693

[22] Filed: Feb. 28, 1995

[51] Int. Cl.$^6$ .......................... A61K 31/00; A61K 33/00; C12N 1/00; C12P 1/04
[52] U.S. Cl. ................... 424/94.1; 424/94.2; 424/94.67; 424/542; 424/600; 424/682; 435/170; 435/252.1; 435/822; 514/906; 514/967; 514/968
[58] Field of Search ................................. 424/94.1, 94.2, 424/94.67, 542, 600, 682; 514/906, 967, 968; 435/170, 252.1, 822

[56] References Cited

U.S. PATENT DOCUMENTS 5,254,338  10/1993  Sakai et al. .......................... 424/78.35
5,344,655   9/1994  Sakai et al. .............................. 424/443

Primary Examiner—John W. Rollins
Assistant Examiner—Deborah K. Ware
Attorney, Agent, or Firm—John G. Costa

[57] ABSTRACT

A common complication of vaginal delivery is the tearing of the muscles of the vagina and perineum. This tearing results in an irregular laceration which the surgeon must then repair. Current obstetrical practice is to prevent this irregular laceration by performing an episiotomy to create a regular laceration which is later sutured. However, both natural tearing of the vaginal and perineal muscles during delivery and surgical episiotomies are subject to further, more grave, complications. The use of medical therapy instead of surgical therapy will reduce the incidence of lacerations of the muscles of the vagina and perineum. The use of medical therapy for the relaxation of the muscles of the vagina and perineum is described.

10 Claims, No Drawings

MEDICAL PREVENTION OF LACERATIONS TO THE VAGINA AND PERINEUM

BACKGROUND

VAGINAL TEARS

During vaginal delivery, lacerations of the vagina and perineum are known to occur. These lacerations have been classified into first, second, third and fourth degree lacerations. A first degree laceration involves the skin and vaginal mucosa but not the underlying fascia and muscle. A second degree laceration further involves the fascia and muscles of the perineum but not the rectal sphincter. A third degree laceration further extends to involve the anal sphincter. A fourth degree laceration further extends through the anal mucosa, thus creating an open communication from the vagina to the lumen of the rectum.

In order to prevent the natural tearing lacerations to the vagina and perineum many, if not most, obstetricians advocate the use of an episiotomy. Although the repair of the natural tear during delivery or of the incision of an episiotomy is virtually the same, the results of suturing the regular incision of an episiotomy tend to be more satisfactory.

EPISIOTOMY

Episiotomy is the most common operation in obstetrics. It substitutes a neat surgical incision for the often jagged laceration that may occur during childbirth. However, some researchers have questioned whether or not there are any advantages to using routine episiotomies. Reynolds and Yudkin (Can Med Assoc J 136:1045, 1987), comparing routine episiotomy with no episiotomy, found that the incidence of second degree lacerations was less with the routine use of episiotomy, but that there was no difference in the incidence of third and fourth degree lacerations. Others have maintained that routine episiotomy is associated with an increased incidence of third and fourth degree lacerations.

The most common puerperal infection is a localized infection of an episiotomy wound. These infections are seldom severe but they are accompanied by pain and dysuria which make the patient uncomfortable. Predictably, serious infections are more likely in women with fourth degree lacerations. Necrotizing fasciitis is a rare but frequently fatal complication of perineal and vaginal wound infections.

As with other surgical procedures aimed at denervation or destruction of muscle, the results with episiotomy are not entirely satisfactory. Although the repair of a surgical incision is certainly easier and initially more satisfactory than the repair of a natural, jagged laceration sustained during childbirth, complications of pain and infection exist whether or not an episiotomy is performed.

The general purpose of episiotomy has been to open the birth canal so that the fetus can pass without forcibly tearing the muscles of the vagina and perineum. The same desired result would be obtained if the muscles involved could stretch, or relax, enough to allow passage of the fetus without tearing of the muscles.

MUSCLE PARALYZING AGENTS

Muscle contracts when it is stimulated by chemical mediators released by nerves. This stimulation is effected by neurotransmitters in the neuromuscular synapse. When a nerve impulse is received at the neuromuscular synapse it causes the presynaptic release of acetylcholine. The post synaptic uptake of acetylcholine then initiates the biochemical reactions leading to contraction of the muscle. Surgical denervation results in the eventual atrophy of muscle. Likewise, chemical denervation, effected by a blocking of the release or uptake of acetylcholine at the neuromuscular junction, will result in changes very similar to the changes of surgical denervation. These changes can be measured.

Botulinum Neurotoxin

One agent known to effect the presynaptic release of acetylcholine is Botulinum Neurotoxin. This neuromuscular blocking agent has been used to alleviate muscle spasm due to excessive neural activity of central origin or to weaken a muscle for therapeutic purposes. Previously, Botulinum Neurotoxin has been found effective and safe for the symptomatic treatment of blepharospasm, strabismus, hemifacial spasm, adductor spasmodic dystonia, spasmodic torticollis, and oromandiular dystonia. Other previously known clinical uses for Botulinum Neurotoxin include detrusor sphincter dyssynergia of the bladder and writer's cramp.

Other investigators are known to be studying the use of the treatment of various disorders, including: focal and segmental limb dystonias, abductor spasmodic dystonia, stuttering, vocal and other tremors, urinary and anal sphincter dysfunction, and the dynamic deformities of cerebral palsy.

The bacterium, Clostridium Botulinum, is known to produce at least seven, A–G, serologically distinct toxins with potent neuroparalytic activity. Serotype A is commercially available and, at least, serotypes B and F are undergoing experimental trials to assess their clinical usefulness and safety. Although antigenically distinct, the seven known toxins have a common structure. The active form, i.e. the form which possesses neuromuscular paralyzing activity, of these toxins is composed of a light chain and a heavy chain linked together by a disulfide bond. The heavy chain determines the binding specificity of the molecule and the light chain determines the toxicity of the molecule. The light chain penetrates the cellular membrane, probably by endocytosis, and acts as an intracellular toxin. It is conceivable that manipulation of the polypeptides of the heavy chain might alter the binding specificity of the molecule and enable a more specific, less clinician dependent, delivery of the toxin to a desired site.

The previous clinical indications for the use of Botulinum Toxin, as outlined in the *National Institutes of Health Consensus Development Conference Statement*, Nov. 12–14, 1990, (NIH Statement), were categorized as uses for Ophthalmic Disorders, Neurologic Disorders, Voice and Speech Disorders, Adductor Spasmodic Dysphonia, Abductor Spasmodic Dysphonia, and Stuttering and Vocal Tremor.

The NIH Statement noted that "safety for use during pregnancy or lactation has not been established". Specific contraindications were noted to be allergy to the drug, infection at the site of injection and inflammation at the site of injection. The exact cause of the development of antibodies is unclear but may be related to the administration of more than 300 units within a 30 day period or to low body weight of the recipient. Several complications are site specific and usually are related to weakness in the injected or adjacent muscles, e.g. transitory fecal incontinence was reported in some patients treated for anismus.

It is of particular importance to note that no objective observation of general weakness has been reported after the therapeutic administration of Botulinum Neurotoxin. Furthermore, in one report, one of nine patients who were pregnant during treatment with Botulinum Neurotoxin gave birth prematurely, but this was not believed to have been due to the use of Botulinum Neurotoxin. By extrapolation from experimental data in primates, it is believed that the $LD_{50}$ in humans is more than 2700 units. When Botulinum Neurotoxin is injected into muscle it is bound at receptor sites on the cholinergic nerve terminal where it blocks the quantal release of acetylcholine. There is evidence of heterogeneity of the receptor sites, including both high and low affinity sites and toxin specific sites. It is believed that the attachment of toxin to acetylcholine vesicles in the terminal nerve endings inhibits calcium dependent exocytosis of acetylcholine. The inhibition of the release of acetylcholine results in muscle paralysis and reversible muscle atrophy. The paralytic effect of Botulinum Neurotoxin is dose related, with a usual onset of clinical effect from one to four (1–4) days after injection and with a peak clinical effect usually occurring from five to ten (5–10) days after injection and a duration of action of usually 12 to twenty weeks, but it may be six months or more. Although the effect is prolonged, it is gradually decreasing. Botulinum Neurotoxin also induces a temporary atrophy in the muscles injected. The effect is also limited in that, clinically, the eventual area of reversible muscle atrophy remains confined to the muscle injected. After injection into the longissimus dorsi muscle of a rabbit, the diffusion gradient of Botulinum Neurotoxin was reported to extend to about 30 mm from the injection site. In humans, however, after the injection of Botulinum Neurotoxin into the sternocleidomastoid muscle, muscle atrophy has been found to extend the entire length of the muscle.

Botulinum toxin type A is currently available in the United States from Allergan Pharmaceuticals and may soon be available from other suppliers as well. A vial containing 100 units of toxin may be gently mixed with from 1 ml of saline to 4 ml of saline to achieve a concentration ranging from 100 U/ml to 25 U/ml as desired. The reconstituted toxin should not be vigorously shaken as this would denature the toxin.

A European preparation also exists and is in clinical use. One unit of the preparation used in the United States is equivalent to about 4–5 units of the preparation used in Europe. For purposes of this specification and the accompanying claims, all Botulinum Neurotoxin units refer to units of the preparation of Botulinum Neurotoxin currently available in the United States from Allergan Pharmaceuticals. All other Botulinum Neurotoxin preparations are incorporated by reference, with the provision that an appropriate adjustment in the number of units of those other preparations used should be made in order to maintain equivalence to the units of the preparation of Botulinum Neurotoxin currently available in the United States from Allergan Pharmaceuticals used in this specification and the accompanying claims.

The dosage of Botulinum Neurotoxin needed for each muscle varies widely. Large, bulky muscles require a larger dose than do smaller muscles. Doses as low as 2.5 units have been used in spasmodic dystonia and doses as high as 400 units have been used in limb and cervical dystonias.

Typically, injection is made with a 1 cc tuberculin syringe fitted with a 26G ½" needle. EMG guided injections are preferred when the muscle to be injected cannot be palpated. The injection of Botulinum Neurotoxin is made through hollow EMG needles such as the 27G 1½" monopolar needle electrodes available from Oculinum, Inc. It is preferred that the amount injected is the least amount of Botulinum Neurotoxin needed to achieve the desired effect.

The effects of Botulinum Neurotoxin can be reversed by the use of antitoxin to the bacterium, Clostridium Botulinum, or by the use of anticholinesterase inhibitors such as physostigmine, or, potentially, by the use of any other agent used in the treatment of Botulism.

Other Muscle Paralyzing Agents

A number of muscle paralyzing agents are known. A review of a standard textbook of pharmacology, such as *Goodman and Gilman's The Pharmacologic Basis of Therapeutics,* eighth edition, 1990, lists a number of such agents. The following is a partial listing of agents compiled mainly from pages 114 and 173 of *Goodman and Gilman,* local anesthetics, tetrodotoxin, saxitoxin, batrachotoxin, hemicholinium, magnesium ions, 4-aminopyridine, curare alkaloids, snake alpha-toxins, calcium inhibitors, decamethonium, veratrine, quinine, metabolic poisons, dantrolene, methacholine, atropine, trimethaphan, and anticholinergic agents. Another agent which has recently been found to paralyze muscle is doxyrubicin.

FIELD OF THE INVENTION

The pelvic diaphragm is formed bilaterally by the fan-shaped levator ani muscles. The levator ani muscles lie deep to the perineal muscles. The perineal muscles most commonly involved in tears during childbirth are the Bulbospongiosus Muscles, the Superficial Transverse Perineal Muscles, the Deep Transverse Perineal Muscles, the Ischiocavernosus Muscles, and the Bulbocavernosus Muscles. Other muscles which are often involved in tears during childbirth are the External Anal Sphincter Muscle, and the Levator Ani Muscles. Other muscles which might be involved in tears during childbirth include the Semitendinosus Muscles, and the Gracilis Muscles.

To prevent tears to the perineum during childbirth, either a mediolateral or midline episiotomy can be performed. Mediolateral episiotomies involve an incision through the vaginal mucosa, the Bulbospongiosus Muscle, the Superficial Transverse Perineal Muscle, and the Deep Transverse Perineal Muscles on one side, and, at times, the superficial fibers of the levator ani muscle on that side.

As the levator ani muscles provide the main support for the bladder, vagina and rectum, it is desirable that these muscles are not severely damaged either by tearing during childbirth or by the surgical incision of episiotomy. It should also be noted that either tearing during childbirth or an episiotomy incision of the external anal sphincter muscle can lead to vaginal-rectal fistulas and other undesirable complications.

It is known that, although muscle tears during childbirth are undesirable and lead to complications, episiotomy is also accompanied by complications.

DESCRIPTION OF THE INVENTION

The purpose of this invention is to offer a medical alternative to episiotomy which will not be plagued by the complications of either the natural muscle tearing of childbirth or the complications of episiotomies.

It is known that muscle atrophy and/or paralysis can be induced by a number of agents. Any one of these agents, either alone or in combination can be used to relax the muscles of the perineum and birth canal, thereby facilitating the passage of the baby during birth, and lessening the incidence of tearing of muscles during childbirth and the need for episiotomy.

The method of administration of a given agent is dependent on the form in which that agent is available, as well as the need to limit the effect of the agent to the muscles involved in childbirth. Combinations of these agents may allow the use of smaller amounts of each individual agent and, hence, have the added advantage of lower toxicity to each individual agent.

PREFERRED EMBODIMENT OF THE INVENTION

In the preferred embodiment of this invention, an effective amount of Botulinum Neurotoxin is injected into at least one muscle chosen from the group of the Bulbospongiosus Muscles, the Superficial Transverse Perineal Muscles, the Deep Transverse Perineal Muscles, the Ischiocavernosus Muscles, and the Bulbocavernosus Muscles.

The administration of Botulinum Neurotoxin is from 1 to 100 days prior to the expected date of childbirth, and preferably from 5 to 14 days prior to the expected date of childbirth and most perferably from 7 to 10 days prior to the expected date of childbirth.

In addition, when desirable, an effective amount of Botulinum Neurotoxin is injected into at least one muscle chosen from the group of muscles consisting of the External Anal Sphincter Muscle and the Levator Ani Muscles. In the event that injection into the Levator Ani Muscle is desired, it is preferable to confine said injection to the superficial fibers of the levator ani muscles. In the alternative, when injection of the Levator Ani Muscles is desirable, it is preferable to avoid injection of Botulinum Neurotoxin into one or more of the muscles chosen from the group of muscles consisting of the Bulbospongiosus Muscles, the Superficial Transverse Perineal Muscles, the Deep Transverse Perineal Muscles, the Semitendinosus Muscles, the Ischiocavernosus Muscles, the Gracilis Muscles, and the Bulbocavernosus Muscles in order to maintain additional support for the underlying structures.

A further alternative is to inject an effective amount of Botulinum Neurotoxin into the Semitendinosus Muscles, and/or the Gracilis Muscles in addition to or instead of injection into other muscles of the perineum.

An effective amount of the currently available, Botulinum Neurotoxin A, is from 10 to 300 units and preferably from 10 to 100 units per muscle. Said injections should be given from 1 to 100 days, and preferably from 7 to 10 days prior to childbirth.

In the event that it is desired to reverse the effects of the Botulinum Neurotoxin, the effects of Botulinum Neurotoxin can be reversed by the use of antitoxin to the bacterium, Clostridium Botulinum, or by the use of anticholinesterase inhibitors, such as physostigmine, or, potentially, by the use of any other agent used in the treatment of Botulism.

It is anticipated in this invention that with the introduction of additional types of Botulinum Neurotoxin into clinical use, the effective amount of and mode of administration of those types of Botulinum Neurotoxin may differ from that used for Botulinum Neurotoxin A. It is further anticipated by this invention that certain agents, in their current form, may not be suitable for the use envisioned by this invention, but that future forms may be suitable, as the pharmacological principles presented here remain the same. For example, an agent which currently can only be administered intravenously with systemic effect may become available in a topical form with limited local effect.

What is claimed is:

1. A method for an alternative to the use of episiotomy during childbirth comprising the administration of an effective amount of a Botulinum Neurotoxin to at least one muscle of the perineum and perianal regions.

2. The method according to claim 1 wherein said at least one muscle is selected from the group consisting of the Bulbospongiosus Muscles, the Superficial Transverse Perineal Muscles, the Deep Transverse Perineal Muscles, the Semitendinosus Muscles, the Ischiocavernosus Muscles, the Gracilis Muscles, the Bulbocavernosus Muscles, the External Anal Sphincter Muscles, and the Levator Ani Muscles.

3. The method according to claim 1 wherein said Botulinum Neurotoxin is Botulinum Neurotoxin Type A.

4. The method of claim 1, wherein said administration is from 1 to 100 days prior to an expected date of childbirth.

5. The method of claim 1, wherein said administration is from 5 to 14 days prior to an expected date of childbirth.

6. The method of claim 1, wherein said administration is from 7 to 10 days prior to an expected date of childbirth.

7. The method of claim 14 wherein said at least one muscle is selected from the group consisting of the Bulbospongiosus Muscles, the Superficial Transverse Perineal Muscles, the Deep Transverse Perineal Muscles, the Ischiocavernosus Muscles, and the Bulbocavernosus Muscles.

8. The method according to claim 1 wherein said at least one muscle is selected from the group of muscles consisting of the External Anal Sphincter Muscle and the Levator Ani Muscles.

9. The method according to claim 1 wherein said at least one muscle is selected from the group of muscles consisting of the Semitendinosus Muscles, and the Gracilis Muscles.

10. The method according to claim 8 wherein any administration of the muscle paralyzing agent, Botulinum Neurotoxin, into the levator ani muscles is confined to the superficial fibers of the levator ani muscles.

\* \* \* \* \*